United States Patent [19]

Siddens et al.

[11] 4,405,529

[45] Sep. 20, 1983

[54] METHOD FOR THE PREPARATION OF DIFLUOROMETHOXYAROMATIC COMPOUNDS

[75] Inventors: Jack K. Siddens, Princeton Junction, N.J.; Sivaraman Raghu, Norwalk, Conn.

[73] Assignee: American Cyanamid Company, Stamford, Conn.

[21] Appl. No.: 420,170

[22] Filed: Sep. 20, 1982

[51] Int. Cl.$^3$ .................. C07C 121/75; C07C 43/225; C07C 69/712; C07C 79/35

[52] U.S. Cl. ............................ 260/465 F; 260/456 R; 260/456 P; 560/55; 560/254; 568/588; 568/649; 568/655; 568/656

[58] Field of Search ............ 260/465 F, 456 R, 456 P; 560/55, 254; 568/588, 649, 655, 656

[56] References Cited

U.S. PATENT DOCUMENTS 4,199,595  4/1980  Berkelhammer et al. .......... 424/304

*Primary Examiner*—Dolph H. Torrence
*Attorney, Agent, or Firm*—Thomas J. Monahan

[57] ABSTRACT

A method for the preparation of certain difluoromethoxyaromatic compounds useful as intermediates in the preparation of pyrethroid pesticides. The method comprises alkylating a p-substituted phenol with excess chlorodifluoromethane at atmospheric or superatmospheric pressures in the presence of a base, water, and an inert water miscible organic solvent or solvent mixtures.

9 Claims, No Drawings

METHOD FOR THE PREPARATION OF DIFLUOROMETHOXYAROMATIC COMPOUNDS

The invention herein described relates to a method for the preparation of various difluoromethoxyaromatic compounds which are useful as intermediates in the preparation of pyrethroid pesticides.

By way of background, pyrethroid pesticides are disclosed in U.S. Pat. No. 4,199,595 which is incorporated herein by way of reference. Some pyrethroids serve as broad spectrum pesticides which are highly effective as contact and stomach poisons against ixodide ticks and a wide variety of insects, (i.e., Dipterous, Lepidopterous, Coleopterous and Homopterous insects). In addition, some pyrethroids exhibit extended residual insecticidal activity on plant tissue and are surprisingly effective for the control of ixodidae. They can be used for the protection of animals against attack by both insects and ixodidae when administered to the animals orally or parenterally or applied thereto as a topical insecticidal or acaricidal formulation.

In light of the beneficial uses of pyrethroid pesticides in the field of agriculture, effective methods for preparing these compounds are highly desirable. An object of this invention is to provide a new and useful method for the preparation of certain difluoromethoxyaromatic compounds which are intermediates in the preparation of pyrethroid pesticides. This object is manifest in the following description and particularly delineated in the appended claims.

More particularly, the present invention relates to a method for the preparation of certain difluoromethoxyaromatic compounds represented by the following structural formula:

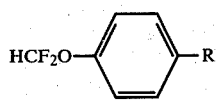
(I)

wherein R is selected from $C_1$–$C_3$ alkyl, halogen, nitro, or is the moiety

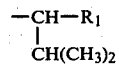

wherein $R_1$ is —CN, —COOR$_2$, OH or OR$_3$, and $R_2$ is $C_1$–$C_3$ alkyl, and $R_3$ is tosyl, mesyl or $C_2$–$C_4$ alkanoyl.

A preferred group of compounds of formula—(I) may be graphically represented and defined by structural formula—(Ia) below:

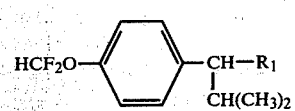
(Ia)

wherein $R_1$ is as hereinabove defined.

Another, more preferred group of compounds is represented by the following structural formula—(Ib):

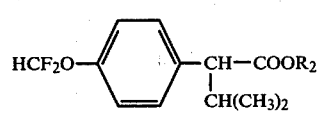
(Ib)

wherein $R_2$ is $CH_3$ or $C_2H_5$.

Of particular interest are the following compounds of formula—(I)

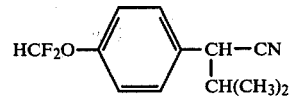

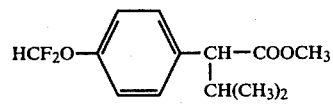

and

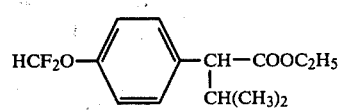

since these are valuable, and convenient, intermediates for the preparation of broad spectrum pyrethroid pesticides.

Advantageously, a compound of formula—(I) may be conveniently prepared by reacting a phenol of formula (II)

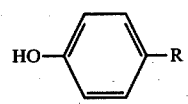
(II)

wherein R is as hereinabove defined, with chlorodifluoromethane at atmospheric or superatmospheric pressures in the presence of a base, water, and an inert water miscible organic solvent or solvent mixtures until the reaction is essentially complete. A compound of formula—(I) is obtained as graphically illustrated below:

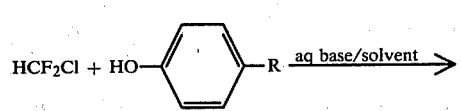

(II)

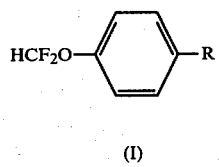

(I)

wherein R is as hereinabove defined.

As stated above, certain of the compounds of formula—(I) are useful and valuable intermediates for the preparation of pyrethroid type pesticides.

Thus, the compounds of formula—(Ia) (i.e., $R_1$=CN or $COOR_2$) may be hydrolyzed to yield the corresponding acid (III). The acid (III) is then converted to the acid chloride (IV), and the acid chloride (IV) is reacted with a benzyl alcohol (V) of structure:

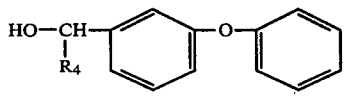

wherein $R_4$ is hydrogen or cyano, to yield the desired pyrethroid insecticide (VI). This reaction sequence may be graphically illustrated as follows:

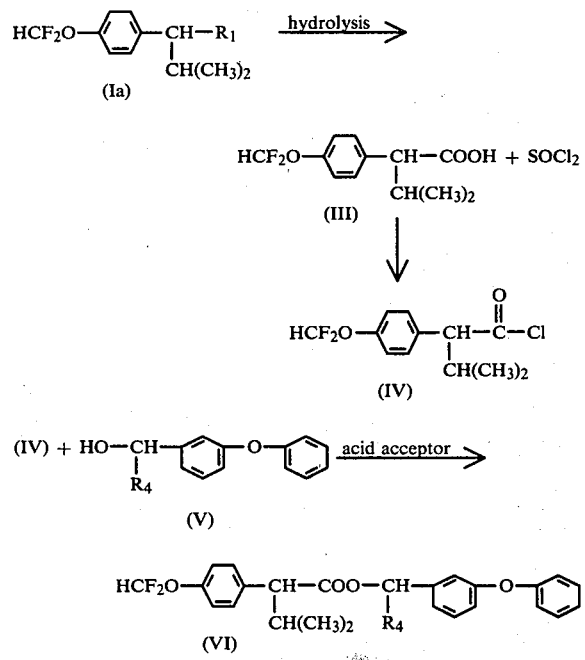

A chiral center is present in formula—(III) acid at the point where the isopropyl group is attached. Thus a d and l isomeric pair is present. A chiral center is also present in the formula—(VI) ester. It is further recognized that when $R_4$ is cyano, a chiral center is present in formula—(V) benzyl alcohol at the point of attachment of the $R_4$ group, thus allowing for an additional chiral center in formula—(VI) pyrethroid when $R_4$ is cyano and resulting in an additional d and l pair.

Conveniently, a compound of formula—(Ia) may be prepared by one method of the present invention as follows:

One molar equivalent of a phenol of formula—(IIa):

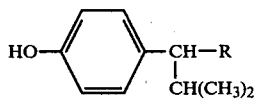

is admixed with and dissolved in a solvent mixture comprising: 2-propanol, and a second solvent selected from acetone or acetonitrile, and water. Water is used in amounts ranging from about 870 to 1740 mole percent water relative to said phenol. In the above reaction mixture the 2-propanol:acetone or 2-propanol:acetonitrile volume ratios are 1:1 to 1:3 and preferably 1:1. The combined volume of these two solvents is in the range of from about 4 to about 6 ml and preferably 4 ml per gram of starting material. The system in which the reaction is to be run is evacuated to remove any air present. Then, chlorodifluoromethane is introduced under a pressure of about 0.4 to 2.5 kg cm$^{-2}$ and preferably 0.45 to 1.1 kg cm$^{-2}$. A few minutes after the start of the reaction one molar equivalent of aqueous sodium hydroxide (preferably 50% aqueous sodium hydroxide) is added resulting in a mild exotherm. After the mild exotherm has subsided, the pressure under which the chlorodifluoromethane is added, is readjusted if necessary to about 1.0 to 1.1 kg cm$^{-2}$. A total of 2 to 3 molar equivalents (preferably three molar equivalents) of chlorodifluoromethane are added to said reaction mixture over a period from about 30 minutes to about 3.0 hours; simultaneously, an additional three molar equivalents of aqueous sodium hydroxide (preferably 50% concentration) are added continuously over approximately the same period of time. The reaction temperature is maintained at a range of from about 20° C. to about 40° C. and preferably 30° to 35° C. Following completion of the base addition, the reaction mixture is held for an additional period of time of from about zero hours to about six hours or until said reaction is essentially complete (preferably from one to two hours). At the end, the total amount of water added is present in the range of from 1740 to 2610 percent relative to the moles of starting material.

The thus obtained product of formula—(I) may be isolated from the reaction mixture by separating the organic phase, which contains said product, from the aqueous and solid phases.

Interestingly, we find, that under similar reaction conditions, excepting that only one organic solvent (i.e., 2-propanol, acetone or acetonitrile) is used, the product yields are markedly lower. Lower yields are also obtained if in the said reaction mixture the amount of water is increased above or decreased below the limits indicated. In fact, the result of a total anhydrous reaction (i.e., sodium hydroxide pellets) is that none or very little compound of formula—(Ia) is formed.

We also recognize that when in the above reaction acetone is substituted for the recommended solvent mixture, at the rate of 4 ml per gram of formula—(II) phenol, and said reaction also contains 10 molar percent of benzyltriethylammonium chloride in conjunction with the acetone, then the yields obtained are comparable to those obtained by the novel process of the present application.

The invention is further described but not limited by the examples set forth below.

EXAMPLE 1

Preparation of Methyl 2-[4-(difluoromethoxy)phenyl]-3-methylbutyrate.

A mixture of methyl 2-(4-hydroxyphenyl)-3-methylbutyrate (44.42 g of 93.8% pure material=41.67 g; 0.20 mol), acetone (83.3 ml), 2-propanol (83.3 ml), and water (62.8 ml) is stirred at 30° C. in a closed system. After the system is evacuated, chlorodifluoromethane is introduced into the reaction mixture under a pressure of 0.49 kg cm$^{-2}$. After about 5 minutes, one equivalent of 50.6% of aqueous sodium hydroxide (10.4 ml; 0.2 mol) from a pressurized reservoir is added all at once causing the reaction mixture to exotherm to 34° C. with a concomitant rise in pressure to 0.7 kg cm$^{-2}$. Slow addition of the rest of 50.6% aqueous sodium hydroxide (31.6 ml; 0.60 mol) then commences and is completed in about 60 minutes. About 5 minutes after the beginning of the slow addition of the base, the pressure under which the chlorodifluoromethane is introduced into the reaction mixture is increased to 1.05 kg cm$^{-2}$. In about 45 minutes a total of 0.60 mol of chlorodifluoromethane (51.66 g) is added. After the addition of the sodium hydroxide is completed, the reaction mixture is stirred for an additional hour. The system is then evacuated to remove any unreacted chlorodifluoromethane from the reaction mixture. Next, a 1:1 mixture (by volume) of acetone:2-propanol (100 ml) is added while washing down the reactor. The reaction mixture is filtered and the organic layer is separated yielding 334.6 g of an orange liquid.

An aliquot (139.44 g; 41.67% of the total) of the above liquid is evaporated under vacuum to remove the solvents. The residue is diluted with toluene (100 ml), and the toluene solution is first washed with 5% aqueous sodium hydroxide (2×75 ml) and then with water (75 ml). It is then evaporated under vacuum to yield 21.26 g of a clear, reddish-orange liquid (calculated yield:

$$\frac{21.26}{41.67} \times 100 = 51.02g \text{ or } 98.9\%).$$

Analysis (glc) indicates this sample to be 86.5% pure corresponding to a real yield of 85.4%.

Another sample prepared by the above method is further purified by vacuum distillation; bp. 58°–59° C. at 0.025 mm Hg.

Analysis

Calculated for $C_{13}H_{16}F_2O_3$:C 60.45; H 6.25; F 14.71; found: C 60.87; H 6.45; F 18.01.

By the above process, a number of experiments are run to evaluate the effect of various solvents, and combinations thereof, alone or in conjunction with other variables on the yields of the product obtained by said process.

In these reactions, the purity of the methyl 2(4-hydroxyphenyl)-3-methylbutyrate is in the range of from about 85% to about 95%. The reactions are run on a 0.2 to 0.3 mole scale at a temperature range of from about 30° to about 35° C., at a pressure range of from 0.49 kg cm$^{-2}$ to 2.45 kg cm$^{-2}$. Under these conditions the chlorodifluoromethane reactant is added over a time period ranging from about 30 minutes to 5.0 hours (in excess amounts as indicated). Following the addition of the aqueous base, the reaction mixtures are held for a time period ranging from 0 to 4 hours (usually 1 hour) under the above-specified conditions prior to workup.

Data obtained as indicated above are summarized in Tables Ia, Ib and Ic.

TABLE Ia

Preparation of Methyl 2-[4-(difluoromethoxy)phenyl]-3-methylbutyrate

| No | Mol % Water added at start | Mol % Water added at end | 2-ProH* | ml of solvent/g of a compound of formula IIa 2nd solvent | ClCHF$_2$ mol equivalent | Product % crude | % purity | % yield |
|---|---|---|---|---|---|---|---|---|
| 1 | 871 | 1740 | 3 | CH$_3$CN 3 | 3.0 | 99.24 | 81.9 | 81.3 |
| 2 | 871 | 1740 | 2 | CH$_3$CN 2 | 3.0 | 97.81 | 82.5 | 80.7 |
| 3 | 1740 | 2611 | 2 | CH$_3$CN 2 | 3.0 | 97.01 | 84.3 | 81.8 |
| 4 | 1740 | 2611 | 2 | acetone 2 | 3.0 | 95.16 | 84.7 | 80.6 |
| 5 | 1740 | 2611 | 2 | acetone 2 | 3.0 | 98.29 | 83.9 | 82.5 |
| 6 | 1740 | 2610 | 2 | acetone 2 | 2.7 | 95.43 | 84.3 | 80.4 |
| 7 | 1740 | 2611 | 2 | acetone 2 | 3.0 | 103.3 | 77.5 | 80.1 |
| 8 | 1740 | 2611 | 1 | acetone 2 | 3.0 | 96.32 | 83.3 | 80.2 |
| 9 | 1740 | 2611 | 2 | acetone 2 | 3.0 | 98.78 | 86.5 | 85.4 |
| 10 | 2614 | 3482 | 2 | acetone 2 | 3.0 | 83.04 | 86.1 | 71.5 |

*2-ProH = 2-propanol

TABLE Ib

Preparation of Methyl 2-[4-(difluoromethoxy)phenyl]-3-methylbutyrate

| No | mol % water added at start | mol % water added at end | ml of solvent/g of a cpd. of formula IIa 2-ProH** | ClCHF$_2$ mol equivalent | Product % crude | % purity | % yield | Remarks |
|---|---|---|---|---|---|---|---|---|
| 1 | 871 | 1740 | 6 | 3.0 | 88.48 | 78.0 | 69.0 | |
| 2 | 871 | 1740 | 6 | 3.0 | 87.00 | 82.2 | 71.5 | |
| 3 | 871 | 1740 | 6 | 3.0 | 98.04 | 78.0 | 76.5 | under 2.45 kg cm$^{-2}$ pressure |
| 4 | 871 | 1740 | 6 | 3.0 | 103.8 | 73.0 | 75.8 | under 2.45 kg cm$^{-2}$ pressure |
| 5 | 871 | 1740 | 6 | 3.0 | 95.21 | 78.3 | 74.5 | under 2.45 kg cm$^{-2}$ pressure |
| 6 | 871 | 1740 | 4 | 2.6 | 80.67 | 86.4 | 69.7 | |

TABLE Ib-continued

Preparation of Methyl 2-[4-(difluoromethoxy)phenyl]-3-methylbutyrate

| No | mol % water added at start | end | ml of solvent/g of a cpd. of formula IIa 2-ProH** | ClCHF$_2$ mol equivalent | Product % crude | % purity | % yield | Remarks |
|----|------|------|---|-----|-------|------|------|---------|
| 7  | 871  | 1740 | 4 | 2.6 | 87.82 | 86.3 | 75.8 | |
| 8  | 871  | 1740 | 6 | 3.0 | 89.02 | 80.5 | 71.7 | |
| 9  | 1740 | 1740 | 6 | 2.9 | 82.88 | 81.2 | 67.3 | ClCHF$_2$ added last after all the base was added |
| 10 | 871  | 1740 | 6 | 3.0 | 79.98 | 84.1 | 67.3 | 10% by wt of * toluene present |
| 11 | 871  | 1740 | 6 | 3.0 | 80.07 | 84.2 | 67.4 | 10% by wt of * toluene present |
| 12 | 871  | 1740 | 6 | 3.0 | 82.73 | 84.0 | 69.5 | 10% by wt of * toluene present |
| 13 | 871  | 1740 | 6 | 3.0 | 83.93 | 83.7 | 70.2 | 10% by wt of * toluene present |
| 14 | 871  | 1740 | 6 | 3.0 | 81.60 | 85.9 | 70.1 | 10% by wt of * toluene present |
| 15 | 871  | 1740 | 6 | 3.0 | 91.90 | 80.7 | 74.2 | 5% by wt of * xylene present |

* = In these preparations the reaction mixture contained the amounts of solvent indicated, simulating the use of solutions of starting material, as isolated from preparative reactions thereof.
**2-ProH = 2-propanol TABLE Ic Preparation of Methyl 2-[4-(difluoromethoxy)phenyl]-3-methylbutyrate

| No | mol % water added at start | end | ml of solvent/g of a cpd. of formula IIa acetone | CH$_3$CN | ClCHF$_2$ mol equivalent | Product % crude | % purity | % yield |
|----|------|------|---|---|-----|-------|------|--------|
| 1 | 1740 | 2610 | 2 | — | 2.3 | 74.32 | 85.5 | 63.5 |
| 2 | 1740 | 2611 | 3 | — | 3.0 | 85.44 | 84.4 | 72.1 |
| 3 | 2614 | 3482 | 4 | — | 3.0 | 73.28 | 85.7 | 62.8* |
| 4 | 1740 | 2611 | 4 | — | 3.0 | 93.16 | 82.5 | 76.9 |
| 5 | 2614 | 3482 | 4 | — | 3.0 | 84.26 | 85.5 | 72.0 |
| 6 | 2614 | 3482 | 4 | — | 3.0 | 82.20 | 85.7 | 70.4** |
| 7 | 871  | 1740 | 6 | — | 3.0 | 97.15 | 81.1 | 78.8 |
| 8 | 871  | 1740 | — | 4 | 3.0 | 97.01 | 80.3 | 77.9 |
| 9 | 871  | 1740 | — | 6 | 3.0 | 95.37 | 78.2 | 74.6 |

*hold time = 0 hr.
**hold time = 5 hr.
Hold time = time of stirring after base addition It can be seen from the above Tables that product yields are improved when mixed solvents (2-propanol:acetone or 2-propanol:acetonitrile) are used in a 1:1 to 1:3 ratio preferably 1:1 ratio, wherein the combined volume of the solvents is in the range of from 4 to 6 ml per gram of starting material. Product yields are lower when the above solvents are used singularly and in amounts from 2 to 6 ml per gram of starting material.

EXAMPLE 2

Preparation of 2-[4-(difluoromethoxy)phenyl]-3-methylbutyronitrile

A mixture of 2-(4-hydroxyphenyl)-3-methylbutyronitrile (25.0 g; 0.1427 mol), 2-propanol (230 ml), and 25.8% aqueous sodium hydroxide (103 ml; 0.857 mol) is stirred in a pressure vessel and chlorodifluoromethane (36.4 g; 0.421 mol) is added over a period of 52 minutes with cooling to control the exotherm and to maintain the temperature of the reaction mixture below 52° C. The reaction mixture is then stirred for an additional 1½ hours. Water (700 ml) and ether (300 ml) are then added to the reaction mixture and the two phase mixture is separated. The ether solution is washed twice with water (1000 ml + 500 ml) and then with saturated brine (300 ml). It is then dried and evaporated under vacuum to yield 30.48 g (94.8%) of a clear, very slightly yellow liquid, shown to be 85.9% pure by gas-liquid chromatography. This corresponds to a yield of 81.4%.

The product is further purified by vacuum distillation, b.p. 106°–109° C. at 0.03 mm Hg.
Analysis Calculated for C$_{12}$H$_{13}$F$_2$NO: C 63.99; H 5.89; N 6.22; F 16.87; found: C 64.02; H 5.90; N 6.38; F 16.95.

By the above procedure, but substituting ethyl 2-(4-hydroxyphenyl)-3-methylbutyrate for 2-(4-hydroxyphenyl)-3-methylbutyronitrile, 2-[4-(difluoromethoxy)phenyl]-3-methylbutyric acid ethyl ester is prepared, respectively. The product is purified by vacuum distillation, b.p. 84.0°–85.5° C. at 0.09 mm Hg.
Analysis
Calculated for C$_{14}$H$_{18}$F$_2$O$_3$: C 61.75; H 6.66; F 13.96; found: C 61.73; H 6.51; F 13.96.

EXAMPLE 3

Preparation of 4-chloro-α,α-difluoroanisole

A mixture of 4-chlorophenol (25.71 g; 0.2 mol), acetone (83.3 ml), 2-propanol (83.3 ml), and water (62.8 ml) is stirred at 30° C. in a closed system. After the system is evacuated, chlorodifuloromethane is introduced into the reaction mixture under a pressure of 0.49 kg cm$^{-2}$. After about 5 minutes, 50.6% aqueous sodium hydroxide (10.4 ml; 0.2 mol) is added at once, followed by the dropwise addition of 50.6% aqueous sodium hydroxide at a rate of approximately 2.6 ml/min. over a period of 59 minutes (total: 31.6 ml; 0.6 mol). Five minutes after the dropwise addition of the base commences, the pressure under which the chlorodifluoromethane is added, is increased to 1.05 kg cm$^{-2}$. In about 55 minutes the addition of chlorodifluoromethane is stopped (a total of 0.6 mol was added). After the addition of the sodium hydroxide, the reaction mixture is stirred for an additional hour.

Next, the system is evacuated to remove unreacted chlorodifluoromethane and about 150 ml of a 1:1 (by volume) mixture of acetone:2-propanol is added as washes of the reactor to the reaction mixture, and the whole is then filtered. After filtration, the organic layer is separated from the aqueous layer and evaporated under vacuum to yield a light orange oil containing some solids. Hexane (200 ml) and water (150 ml) are added to the oil. The hexane layer is washed with 5% aqueous sodium hydroxide (150 ml), dried and evaporated under vacuum to yield 24.63 g (69%) of a clear, yellow oil. The oil is vacuum distilled to yield the product, b.p. 61.5°–63.0° C. at 15–25 mm Hg.

Analysis

Calculated for $C_7H_5ClF_2O$: C 47.08; H 2.82; Cl 19.86; F 21.28; found: C 47.08; H 2.85; Cl 20.05; F 21.05.

By the above procedure, but substituting p-cresol for 4-chlorophenol, α,α-difluoro-4-methylanisole is obtained, respectively, b.p. 52.5°–53.5° C. at 15–25 mm Hg.

EXAMPLE 4

Preparation of α,α-difluoro-4-nitroanisole

The procedure of Example 3 is used, except that 4-nitrophenol is substituted for 4-chlorophenol.

The organic layer is evaporated under vacuum. The residue obtained is taken up in a mixture of hexane (150 ml) and water (150 ml) but it is only partially soluble in same. The mixture is filtered to yield 28.2 g (74%) of a slightly yellow solid. On evaporation, the hexane layer yields 3.88 g (10.3%) of a solid. The fractions are combined and recrystallized from a hexane-methylene chloride mixture, mp 32.5°–35.5° C. [reported mp 32°–32.5° C.; T. G. Miller and J. W. Thanassi, J. Org. Chem. 25: p. 2009 (1960)].

What is claimed is:

1. A method for the preparation of a compound of the structural formula:

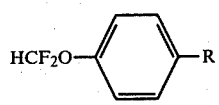
(I)

wherein R is $C_1$–$C_3$ alkyl, halogen, nitro, or R is the moiety

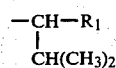

wherein $R_1$ is CN, COOR$_2$, OH, or OR$_3$, $R_2$ is $C_1$–$C_3$ alkyl, and $R_3$ is tosyl, mesyl, or $C_2$–$C_4$ alkanoyl, comprising: reacting one molar equivalent of a compound of structural formula

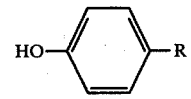
(II)

wherein R is as hereinabove defined, at a temperature ranging from approximately 20° to 40° C., in a solvent mixture, of 2-propanol:acetonitrile or 2-propanol:acetone wherein said solvent mixture contains the above solvents in 1:1 to 1:3 volume ratios and said solvent mixture is used in amounts of from 4 to 6 ml per gram of the compound of formula—(II) and in the initial presence of from approximately 870 to 1740 mol percent of water, with two to three molar equivalents of chlorodifluoromethane added under a pressure of from 0.4 to 2.5 kg cm$^{-2}$ over a period of time ranging from approximately 30 minutes to 3.0 hours and with an aqueous solution of four molar equivalents of an alkali metal hydroxide of sodium or potassium hydroxide, wherein the concentration of said aqueous solution is such that on completion of the base addition the total amount of water added in the reaction mixture is of from approximately 1740 to 2610 mol percent, is added essentially simultaneously with the chlorodifluoromethane addition over a period of time ranging from approximately 1.0 to 5.0 hours, and on completion of the base addition the reaction mixture is further maintained at the above pressure and temperature ranges for a period of time of from 0 to 6 hours, or until said reaction is essentially complete.

2. A method according to claim 1, wherein to a solution at a temperature of from 30° to 35° C. of one molar equivalents of a compound of formula—(II) in a solvent mixture of 2-propanol:acetone wherein the volume ratio of said solvent is 1:1 and in the total volume amount of 4 ml per gram of a compound of formula—(I) and water which is added initially at the rate of 1740 mole percent is added 3 molar equivalents of chlorodifluoromethane over a time period ranging from 30 minutes to 1.0 hour at a pressure of from approximately 0.4 kg cm$^{-2}$ to 1.1 kg cm$^{-2}$ along with initially the simultaneous addition of 4 molar equivalents of an aqueous sodium hydroxide solution which is added over a period of time of approximately 1.0 hour to 2.0 hours, and on the completion of the base addition, the total amount of water added is 2610 mol percent and the reaction is further maintained at the above pressure and temperature range for a period of time of from approximately 1 to 2 hours.

3. A method according to claim 2, wherein R is CH$_3$, Cl, NO$_2$or

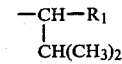

and $R_1$ is CN, COOCH$_3$ or COOC$_2$H$_5$.

4. A method according to claim 3, wherein said compound is methyl 2-[4-(difluoromethoxy)phenyl]-3-methylbutyrate.

5. A method according to claim 3, wherein said compound is ethyl 2-[4-(difluoromethoxy)phenyl]-3-methylbutyrate.

6. A method according to claim 3 wherein said compound is 2-[4-(difluoromethoxy)phenyl]-3-methylbutyronitrile.

7. A method according to claim 3, wherein said compound is 4-chloro-α,α-difluoroanisole.

8. A method according to claim 3, wherein said compound is α,α-difluoro-4-methylanisole.

9. A method according to claim 3, wherein said compound is α,α-difluoro-4-nitroanisole.

* * * * *